United States Patent [19]

Tulaszewski

[11] 4,232,681
[45] Nov. 11, 1980

[54] LEG POSITIONING DEVICE FOR X-RAY FILMING

[76] Inventor: Olaf Tulaszewski, Friedrich-Ebert-Str. 25, 6103 Griesheim near Darmstadt, Fed. Rep. of Germany

[21] Appl. No.: 955,962

[22] Filed: Oct. 30, 1978

[30] Foreign Application Priority Data

May 16, 1978 [DE] Fed. Rep. of Germany ....... 2821251

[51] Int. Cl.³ .............................................. A61B 6/00
[52] U.S. Cl. ...................................... 128/653; 128/69; 128/133; 250/439 R; 269/328
[58] Field of Search ................. 128/1 R, 653, 654, 69, 128/133, 20; 250/439 R, 451, 456; 269/322, 328

[56] References Cited

U.S. PATENT DOCUMENTS

| 32,014 | 4/1861 | Taylor | 128/69 UX |
|---|---|---|---|
| 965,195 | 7/1910 | Kelley | 250/451 |
| 1,980,848 | 11/1934 | Cass | 269/328 |
| 2,829,640 | 4/1958 | Moorman | 269/328 X |
| 3,092,079 | 6/1963 | Strebel et al. | 269/328 X |
| 3,521,876 | 7/1970 | Smith | 250/456 |
| 3,915,153 | 10/1975 | Quinn | 250/439 X |
| 4,069,813 | 1/1978 | Gilula | 128/654 |

OTHER PUBLICATIONS

*Helv. Chir. Acta,* 43, 195–203, 1976.
*Tables by Tower,* Catalogue of the Tower Co., Feb., 1951, p. 7.

*Primary Examiner*—Kyle L. Howell
*Attorney, Agent, or Firm*—Michael J. Striker

[57] ABSTRACT

A leg positioning device for X-ray filming has a support with which the leg can be fixedly held at two spaced locations, a pressure element which can apply incrementally variable pressure to the leg intermediate these locations, and a device for measuring the applied pressure so that the same can be exactly reproduced whenever desired.

13 Claims, 7 Drawing Figures

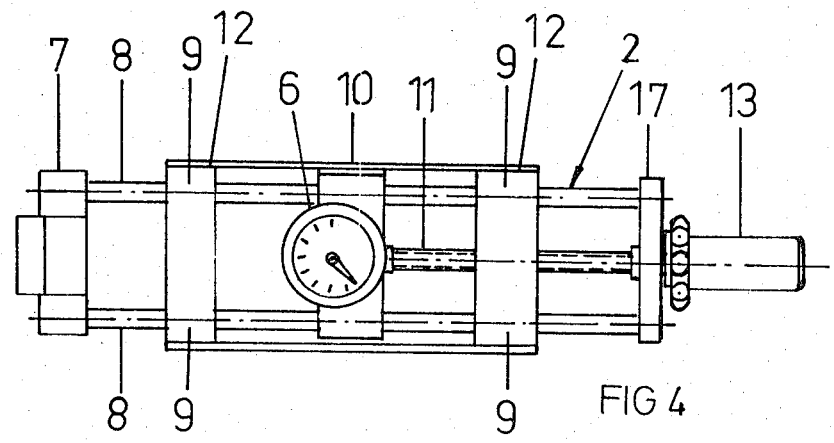
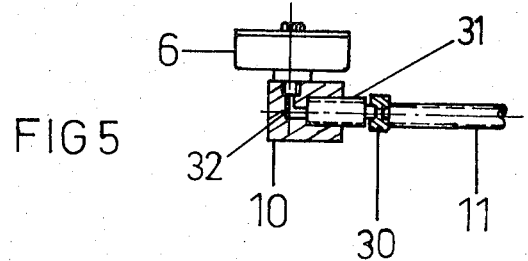
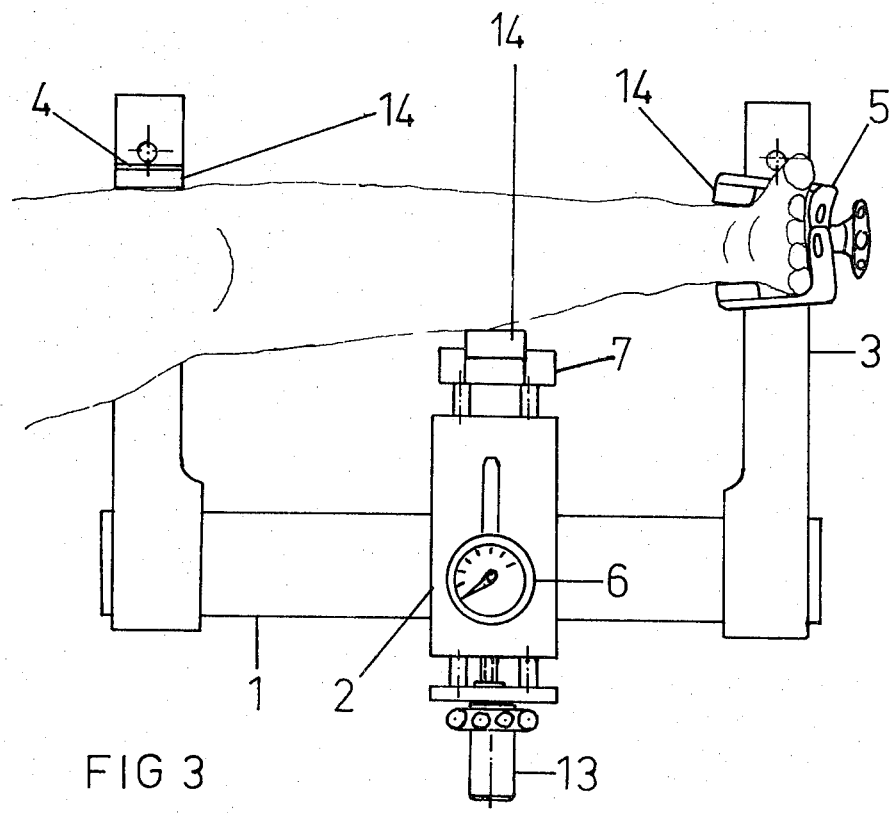

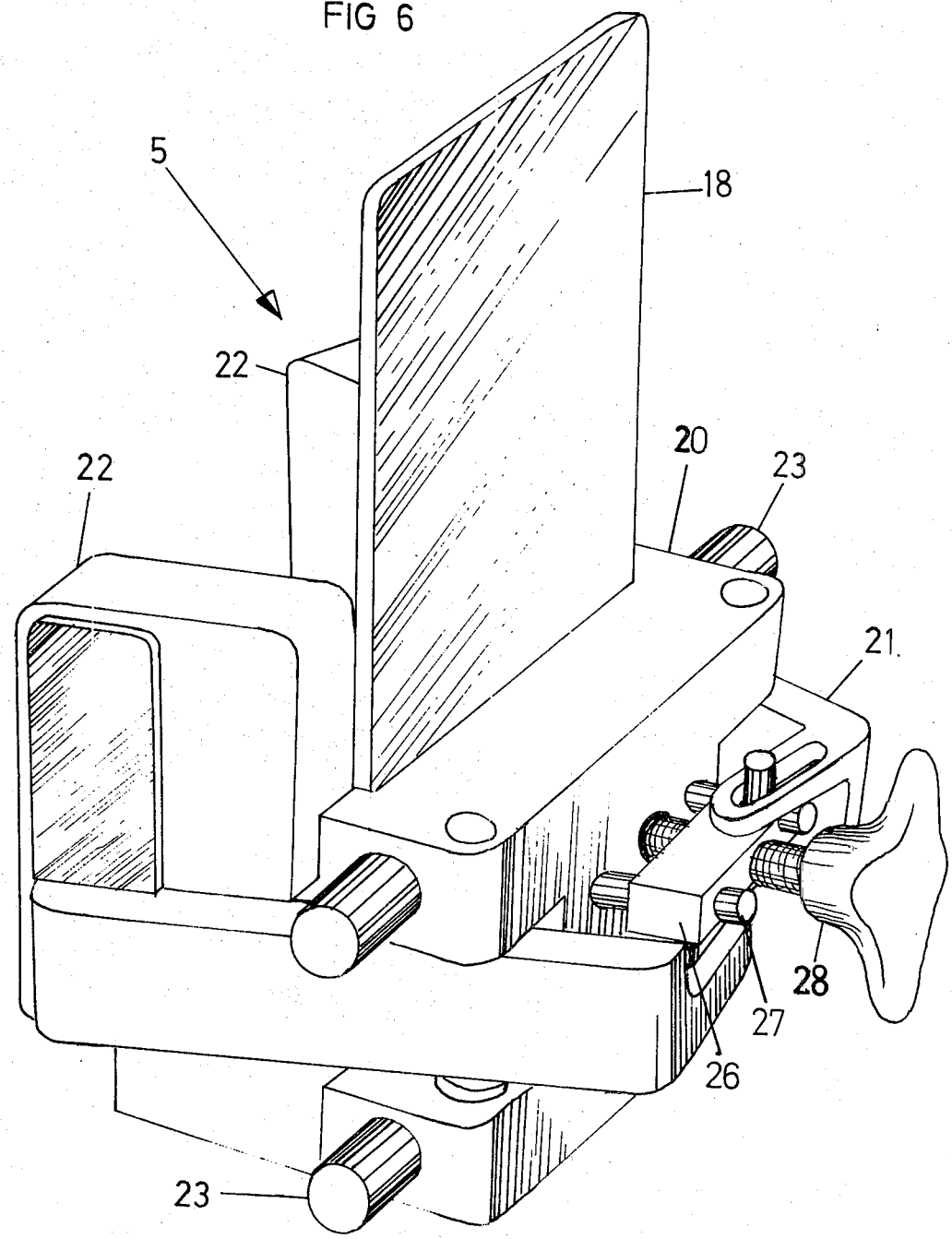

LEG POSITIONING DEVICE FOR X-RAY FILMING

BACKGROUND OF THE INVENTION

1. Field of the Invention

This invention relates to a device for positioning human legs in preparation for the taking of X-ray films.

More particularly, the invention relates to a device of the above character which permits the taking of X-ray films of legs held in forced extreme joint positions, especially for the purpose of diagnosing ligamentous damage.

2. The Prior Art

Certain diagnostic X-ray examinations of the human leg can be made only when the leg is held in specific, defined positions. This is particularly true of the diagnosis of ligamentous lesions (i.e., ruptures of the ligaments) in the leg. A device for holding the leg for this purpose has been described in Helv. CHIR. ACTA 43, 195–203, 1976. In this device the lower part of the leg is placed on a tubular steel bracket and the heel rests in a V-shaped bracket which is secured to and projects laterally from, a leg board. On the other side of the board, as considered with reference to the foot, a member is mounted which can be turned in opposite directions, depending upon which leg is being examined, so as to properly position an ankle joint in the path of laterally impinging X-rays. Laterally mounted on the board is a holder for the X-ray film. Two straps on the tubular steel bracket serve to urge the lower part of the leg downwardly with respect to the fixedly positioned foot.

This prior art device is suitable for exposing relative displacements of talus and fibia (known as the "drawer phenomenon") to the X-ray equipmemt, and to show that (or whether) there has been damage to the ligamentum fibulo talare anterius.

There are, however, two problems: the device cannot be used to provide exact proof as to whether damage has been sustained to the ligamentum fibulo calcaneare, and the degree of displacement between talus and fibia depends upon the pressure exerted by the straps. Since this pressure cannot be reproduced exactly on the occasion of different examinations, it follows that the original X-ray picture also cannot be exactly reproduced. This, however, is necessary to permit comparison pictures to be made of the other, healthy foot and to enable the diagnostician to compare a final, post-treatment X-ray with the original picture to draw conclusions as to the corrective results obtained.

SUMMARY OF THE INVENTION

Accordingly, it is an object of the invention to provide further improvements over the prior art.

More particularly, it is an object of the invention to provide a leg positioning device which is able to so position a leg as to make it possible to take X-ray pictures proving or disproving the existence of damage to the ligamenti fibulo talare anterius and posterius, of the ligamentum deltoideum, of the lateral ligaments of the knee and of the anterior crossed ligament.

Another object is to provide a device of the type in question which permits the position of the leg to be exactly reproduced on different occasions, so that X-ray films taken on these different occasions will also be equally well reproduced.

In pursuance of these objects and of others which will become apparent hereafter, one feature of the invention resides in a leg positioning device for X-ray filming. Briefly stated, the device may comprise supporting means, including an elongated guide member, a pair of laterally projecting outriggers mounted on respective end positions of the guide member for sliding movement lengthwise thereof, and a plurality of leg-engaging and retaining elements on the respective outriggers, so that a leg engaged by the elements extends lengthwise of the guide member from one to the other of the outriggers; and pressure-means for applying to the engaged leg intermediate the elements reproducible pressure acting in direction transversely of the elongation of the guide member and hence of the leg.

The device according to the invention can be placed on the X-ray table of any X-ray installation; this assures that the plane of filming is always the same and the installation need not be tilted. The need for a separate film holder is eliminated since the cassette containing the X-ray film can simply be placed below the inventive device or, in the event of automatic exposure, can be placed into the X-ray table.

Because the device is adjustable in longitudinal as well as in transverse direction, and because the element which applies pressure to the leg can be slidably adjusted, the novel device can be set for all leg- and foot sizes. The pressure meter allows exact comparison of the load on the left and right legs of a patient and the results are exactly reproduceable during later re-examinations.

BRIEF DESCRIPTION OF THE DRAWING

FIG. 3 is a top plan view of the device shown in FIG. 1, with a leg inserted into the device so as to be held by the same;

FIG. 4 is a top-plan view of another component of FIG. 1, shown on an enlarged scale;

FIG. 5 is a fragmentary longitudinal section through the component in FIG. 4;

FIG. 6 is an enlarged perspective view, showing the foot-supporting component of the device in FIG. 1.

DESCRIPTION OF THE PREFERRED EMBODIMENTS

Figure 1:
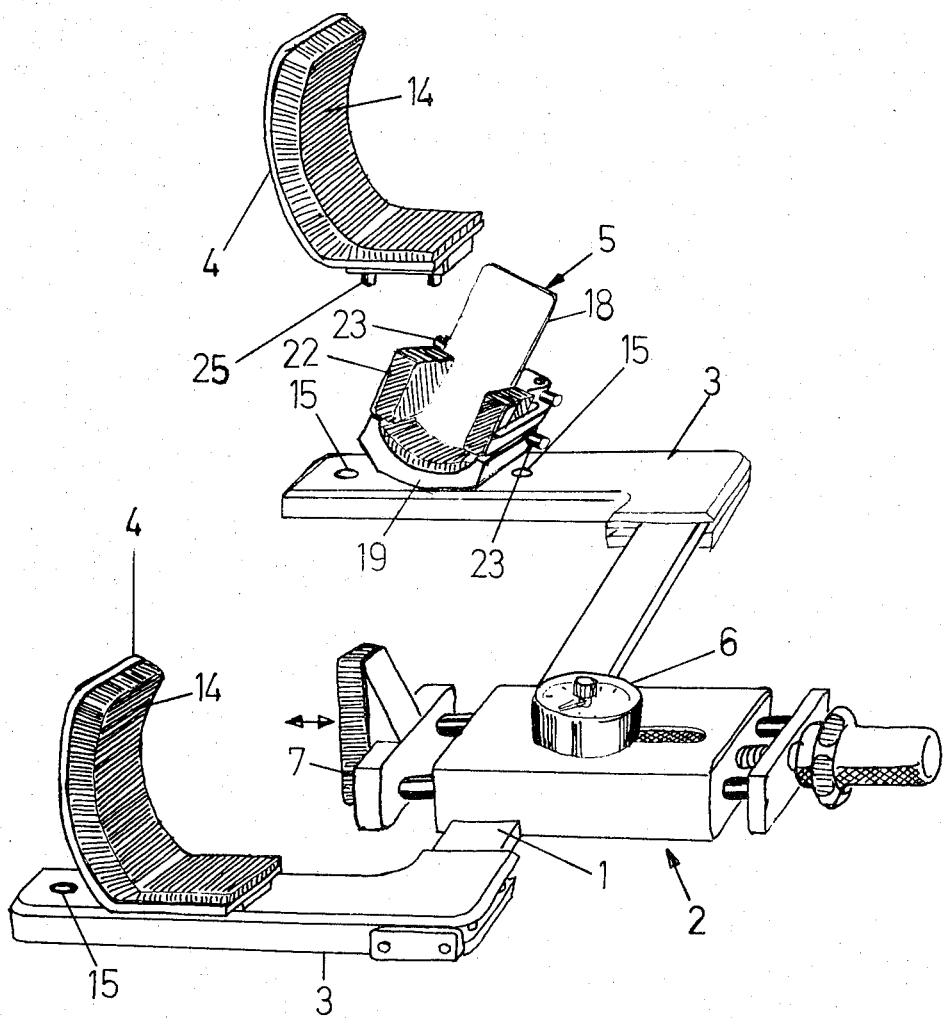
FIG. 1 is a perspective view of a device according to the invention.
Figure 2:
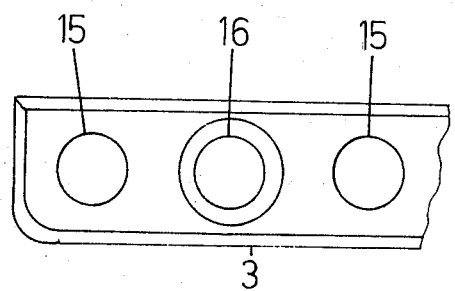
FIG. 2 is a fragmentary view of a component of FIG. 1, on an enlarged scale.

The exemplary embodiment of the device shown in FIGS. 1–7 comprises a rail 1 (which may simply be a flat bar) and a support 2 which is mounted on the rail 1 for shifting along the same. The opposite end portions of the rail 1 are provided with outriggers 3 each of which has three or more holes 15, 16 (not all of these are visible in FIG. 1) to receive pins on holding members 4, 5 which are to support the shank of the leg and the foot, respectively (see FIG. 3). As shown in FIG. 2, the holes 15 are simply bores, whereas the hole 16 has an anti-friction bearing installed in it, as indicated by the double circular line).

The holding member 4 which is mounted on the outrigger 3 at the bottom of FIG. 1 is of C-shaped configuration and provided with pins 25 for insertion into the holes of the outrigger. The holding member 5 mounted on the outrigger 3 at the top of FIG. 1 is a different type, having a foot-support plate 18 and a heel support 19, as well as two lateral pivotable sideparts 22. The member 5 is mounted on its outrigger with a single pin 24 (see FIG. 7). In place of member 5, a second holding member 4 can be mounted on this upper outrigger, as suggested by the illustration of the second member 4 in FIG. 1.

Figure 7:
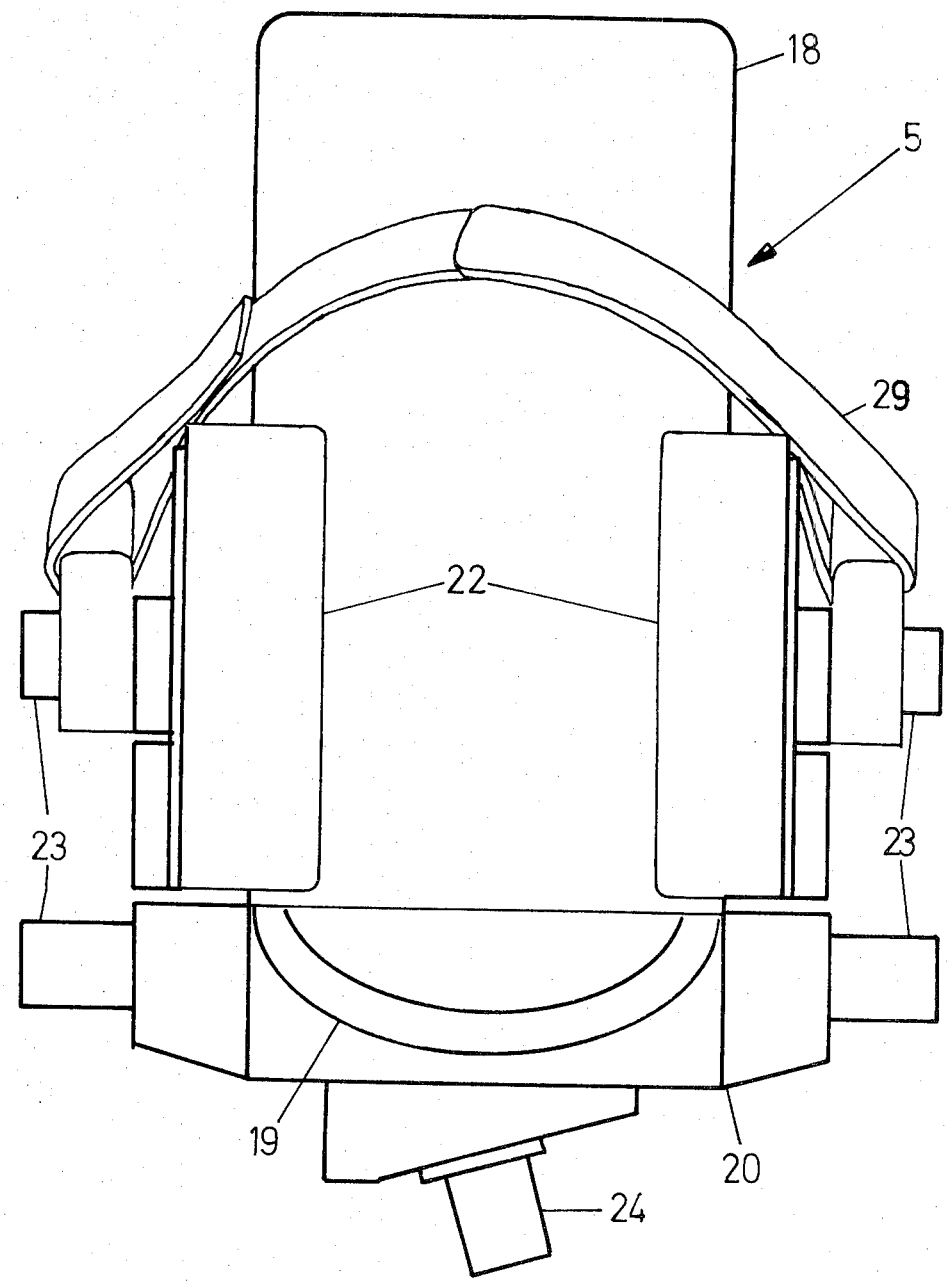
FIG. 7 is a front elevation of the component in FIG. 6, looking towards the right in that Figure.

As shown in more and larger detail in FIGS. 6 and 7, the holding member 5 for the patient's foot includes a part 20 in which the sideparts 22 are pivotably journalled. The foot-support plate 18 and the heel support 19 are secured to the front of part 20. At its lateral sides the part 20 is provided with respective pairs of pins 23; the pins of each pair have the same on-center spacing from one another as do the holes 15 of the outrigger 3 (compare FIG. 2). The lower side (i.e., the bottom surface) of part 20 is provided with the already mentioned single pin 24 (FIG. 7) which is inclined with reference to the longitudinal axis of the holding member (i.e., with reference to the plane of the bottom surface) by e.g., 20°. Actually, the angle of inclination may be between substantially 10°–30°. When the pin 24 is inserted into the hole 16 provided with the anti-friction bearing, the holding element 5 can be turned on the associated outrigger 3 through 360°. The longitudinal axis of the holding member 5 (imaginary, not shown) circumscribes during such rotation an upwardly open cone. When one pair of pins 23 is inserted into the holes 15 the member 5 is fixed and faces in one lateral direction, and when the other pair of pins 23 is instead inserted into the same holes the member 5 is again fixed, but faces in the opposite direction.

FIG. 6 shows most clearly that the sideparts 22 are coupled via the illustrated slot-and-pin connections with a slide member 26 which is provided with two parallel bores through which respective parallel rods 27 extend whose front ends are connected to (e.g., by threading or welding) the part 20. The member 26 can thus slide on the rods 27 lengthwise of the same. This sliding displacement is effected by a bolt or threaded rod 28 (preferably having the illustrated gripping knob to facilitate its turning) which extends through a tapped center hole of member 26 and meshes with the thread therein, and which is turnably mounted in the part 20. A retaining strap 29 is shown in FIG. 7 (omitted from FIGS. 1 and 6 for clarity) which serves to retain the foot, especially in the event that the foot is strongly swollen.

Details of the support 2 are shown in FIGS. 4 and 5, from which it will be seen that the support includes a frame 12 in which two bearing blocks 9 are mounted. Two rods 8 extend parallel to one another through respective bores in the blocks 9 and are connected to one another at one end by a pressure-exerting member 7 and at the other end by a traverse 17. A further guidance of the rods 8 is effected substantially midway between the blocks 9, by means of another traverse 10.

Between and parallel to the rods 8 there is provided a screw spindle 11 which is guided for rotation in the block 9 closest to the traverse 17; it also extends through the traverse 17 but with sufficient freedom to permit relative longitudinal displacement of traverse 17 and spindle 11. A small hydraulic cylinder 31 is mounted on the traverse 10 (FIG. 5) and the tip of screw spindle 11 bears upon the piston of the cylinder 31 via a coupling member 30. The interior of the cylinder is in turn in communication with a dial gauge 6 on traverse 10, via an angled bore in the latter.

In this construction, turning of the spindle 11 via the handwheel 13 causes the part 7 to be advanced or retracted, respectively, as indicated by the double-headed arrow in FIG. 1. When during such advancement the member 7 encounters back pressure (as it bears against a leg as shown in FIG. 3), this is communicated to the cylinder 31 and via the same to the dial gauge 6 which indicates the pressure value on its dial. Thus, the pressure setting is always exactly reproducable. It is advantageous, but not absolutely necessary, if the gauge 6 is of the type (well known in the art) which has a drag-type pointer, i.e., a pointer which remains in the indicating position even after the pressure has been removed so that the indicated value remains visible (such pointers are then later released by e.g., depressing a button to free them).

For the comfort of the patient all parts of the device which came in contact with the leg or foot are provided with a cover 14 which is elastically yieldable (e.g., foam rubber) but must of course be permeable to X-rays. This is shown in FIG. 1.

To make an X-ray diagnosis of new or old ruptures of the fibular ligaments, of the lateral ligaments of the knee or of the anterior crossed ligament, the apparatus is used in the following manner, reference being had to the general illustration provided in FIG. 3:

The leg to be examined is placed into the device so that the knee region is supported by the member 5 which fixes the foot due to engagement of the foot with the support plate 18, the heel support 19 and the lateral supports 22. Of course, positioning and holding of the leg, as well as the place where pressure is applied via the member 7, will differ in dependence upon the injury.

In the event of injury to the ligamentum fibulo talare anterius, the shank of the leg and the foot will be inserted laterally (sole of the foot parallel to the X-ray table at a 90° angle to the X-ray path) into the device, the member 5 holding the foot and the member 4 engaging the shank at about the level of the knee. The pressure member 7 presses on the tibia immediately above (i.e., close to) the foot. The relative shift (drawer phenomenon) between talus and tibia in the lateral X-ray path permits an objective diagnosis of damage to the ligamentum fibulo talare anterius.

If injury to the ligamentum fibulo calcaneare is suspected, the foot is held in the device for anterior-posterior X-ray examination, with the foot so rotated as to extend at a 20° angle to a line normal to the surface of the X-ray table. The shank is placed with its outer side against the member 4, the foot is placed into the member 5, and pressure is exerted with the member 7 upon the tibia above the inner side of the tarsal joint. If a rupture of the ligamentum fibulo calcaneare exists, this will be visible on the X-rays as a displacement (folding-open) between talus and tibia in excess of 7°.

When injury to the ligamentum deltoideium is to be examined the shank is inserted into the device in a position which is mirror-reversed with reference to the one described in the preceding paragraph. The member 7 then exerts pressure on the tibia above the outer side of the tarsal joint and again the pressure of damage will be revealed as a displacement (folding-open) between talus and tibia.

To examine for injury of the anterior crossed ligament, the leg is inserted laterally into the device. The member 5 is replaced with the second member 4 in this case, so that the members 4 engage the leg above the foot and partly on the patella, respectively. The member 7 presses against the shank from behind the leg. In the event of damage to the anterior crossed ligament, a clear indication of relative frontal displacement (drawer phenomenon) between talus and tibia will be visible in the X-rays.

In the event of injury to the inner lateral ligament of the knee, the patient is requested to draw up his leg until it forms an angle of about 10°-15° with the body. In this position the leg is inserted into the device and is held by the two members 4 (the member 5 is not used and is consequently replaced by the second member 4) which engage at about the middle of the inner side of the thigh and at about the middle of the inner side of the shank. The member 7 is then made to exert pressure against the outer side of the knee.

Conversely, in the event of injury to the outer lateral ligament of the knee, the two members 4 are used to engage the leg at about the middle of the outer side of the thigh and at about the middle of the outer side of the shank, and the member 7 is made to exert pressure upon the inner side of the knee (the hollow of the knee) in outward direction. Injury to either of the lateral ligaments of the knee manifests itself in the X-ray films by the angle included between the tibia and the femur.

The leg and foot can be held in all the necessary different positions because of the interchangeability of the members 4, 5 and because of the possibility to make exchanges from left to right position, and vice versa (i.e., by inserting the pins of the respective member into the holes 15 with the members 4, 5 facing either left or right in FIG. 1). Because the leg and foot will always be held in precisely defined positions, and because the pressure exerted with the element 7 can always be exactly duplicated on the basis of the pressure reading obtained from dial gauge 6, the X-ray pictures obtained of one and the same leg at different points in time (e.g., for the initial diagnosis and for a later reexamination) will always be taken under identically reproduceable conditions, so that a true and valid comparison is possible.

The disclosed invention is susceptible of various modifications. For example, the number of holes 15, 16 could differ from the one shown in the drawing. The anti-friction bearing in hole 16 could be eliminated but this would make turning of the member 5 somewhat more difficult. The support 2 could be constructed differently than illustrated and an indicating instrument other than a dial gauge (e.g., a strain gauge with digital read-out, as known per se in other arts) could be employed. Should a differently constructed support be used, then it is essential to ensure that the pressure applied to the leg via the element 7 or its equivalent can be increased very gradually and in small increments, to avoid causing the patient pain and discomfort by applying too much pressure too quickly to the traumatized joint.

While the invention has been illustrated and described as embodied in a leg positioning device for X-ray filming, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A leg positioning device for X-ray filming, comprising supporting means, including an elongated guide member, a pair of laterally projecting outriggers mounted on respective end portions of said guide member for sliding movement lengthwise thereof, and a plurality of leg-engaging and retaining elements on the respective outriggers, so that a leg engaged by said elements extends lengthwise of said guide member from one to the other of said outriggers, said elements comprising one member for engaging and retaining a foot of the leg, and a pair of members for engaging and retaining the leg above the foot, any two of said members being jointly usable at one time; and pressure means for applying to the engaged leg intermediate said elements reproducible pressure acting in direction transversely of the elongation of said guide member and hence of the leg, said pressure means comprising a pressure-exerting pusher component, mounting means mounting said pusher component on said guide member for movement lengthwise of the elongation of the same as well as transverse to said elongation toward and away from an engaged leg, and means for measuring and visually indicating the pressure which is being exerted by said pusher component upon the leg.

2. A device as defined in claim 1, and further comprising means for mounting the respective members on said outriggers in a plurality of different orientations relative thereto.

3. A device as defined in claim 1, said members of said pair of members each including a substantially C-shaped bracket having one leg provided on an outer surface thereof with a plurality of pins insertable into holes of the outriggers, said bracket having an inner leg-engaging surface provided with padding.

4. A leg positioning device for X-ray filming, comprising supporting means, including an elongated guide member, a pair of laterally projecting outriggers mounted on respective end portions of said guide member for sliding movement lengthwise thereof, and a plurality of leg-engaging and retaining elements on the respective outriggers, so that a leg engaged by said elements extends lengthwise of said guide member from one to the other of said outriggers, said elements comprising one member for engaging and retaining a foot of the leg, and a pair of members for engaging and retaining the leg above the foot, any two of said members being jointly usable at one time; said one member comprising a heel-support portion, a sole-support portion projecting from said heel-support portion, a pair of lateral support portions engageable with the lateral sides of a foot, a single pin beneath said heel support portion for insertion into a hole of the respective outrigger so that the one member can be turned about an axis defined by the pin, and two pairs of pins at respective lateral sides of said one member and receivable in additional holes of the respective outrigger to fixedly secure said one member thereto in respective different orientations; and pressure means for applying to the engaged leg intermediate said elements reproducible pressure acting in direction transversely of the elongation of said guide member and hence of the leg.

5. A device as defined in claim 4, said one member further comprising a bridge part in which said lateral support portions are pivotably journalled, a threaded element connected to said bridge part, and means coupling said lateral support portions with said threaded element so that said lateral support portions are pivoted towards and away from the respective lateral sides of a foot in dependence upon the direction in which said threaded element is turned.

6. A device as defined in claim 4, said outriggers each having a plurality of holes to receive the respective pins, at least one of said holes housing an anti-friction bearing in which said single pin of said one member is receivable.

7. A device as defined in claim 4, said heel support portion having a bottom surface, and said single pin projecting downwardly from said bottom surface and including with the same an angle between substantially 10°–30°.

8. A leg positioning device for X-ray filming, comprising supporting means, including an elongated guide member, a pair of laterally projecting outriggers mounted on respective end portions of said guide member for sliding movement lengthwise thereof, and a plurality of leg-engaging and retaining elements on the respective outriggers, so that a leg engaged by said elements extends lengthwise of said guide member from one to the other of said outriggers; and pressure means for applying to the engaged leg intermediate said elements reproducible pressure acting in direction transversely of the elongation of said guide member and hence of the leg, said pressure means comprising a mounting element on said guide member, a pressure-exerting element, a screw-spindle carrying said pressure-exerting element and being mounted in said mounting element for longitudinal displacement therein transversely to the elongation of said guide member toward and away from an engaged leg, and means intermediate said pressure-exerting element and said screw spindle for measuring the pressure exerted by the former upon a leg.

9. A device as defined in claim 8, said mounting element including a frame, a pair of bearing blocks mounted in said frame spaced from one another, a first traverse in said frame intermediate the spaced bearing blocks, a pair of parallel rods extending through said bearing blocks and having first end portions projecting beyond one of the same and said end portions projecting beyond the other bearing block and both connected to said pressure-exerting element, a second traverse connecting said end portions, and means for shifting said second traverse with said rods towards and away from said first traverse and for thereby advancing and retracting said pressure-exerting element.

10. A device as defined in claim 9, said shifting means comprising a screw spindle turnably journalled in said one bearing block and extending freely through a hole in said second traverse, said pressure-measuring means being mounted on said first traverse and said screw spindle having a free end coupled with said pressure-measuring means in pressure-transmitting relationship.

11. A device as defined in claim 10, said pressure-measuring means comprising a dial gauge.

12. A device as defined in claim 10, said pressure-measuring means comprising a hydraulic cylinder-and-piston unit having a fluid-filled interior and a piston, and a dial gauge operatively connected with said fluid-filled interior, said free end of said screw spindle bearing upon and displacing said cylinder when said screw spindle is turned in one direction.

13. A device as defined in claim 12, said dial gauge having a drag-type pointer.

* * * * *